(12) United States Patent
He

(10) Patent No.: US 11,000,612 B1
(45) Date of Patent: May 11, 2021

(54) OZONE DISINFECTION DEVICE FOR ACTIVELY REMOVING OZONE, OZONE DISINFECTION SYSTEM, AND OZONE DISINFECTION METHOD

(71) Applicant: DCSTAR INC, New York, NY (US)

(72) Inventor: Ligui He, New York, NY (US)

(73) Assignee: DCSTAR INC, New York, NY (US)

( * ) Notice: Subject to any disclaimer, the term of this patent is extended or adjusted under 35 U.S.C. 154(b) by 0 days.

(21) Appl. No.: 16/931,172

(22) Filed: Jul. 16, 2020

(51) Int. Cl.
  *A61L 9/00* (2006.01)
  *A61L 2/20* (2006.01)

(52) U.S. Cl.
  CPC ......... *A61L 2/202* (2013.01); *A61L 2202/121* (2013.01); *A61L 2202/122* (2013.01); *A61L 2202/14* (2013.01); *A61L 2202/15* (2013.01); *A61L 2202/24* (2013.01)

(58) Field of Classification Search
  CPC ... A61L 2/20; A61L 2/202; A61L 2/24; A61L 2202/122; A61L 2202/123; A61L 2202/13
  USPC ................. 422/28, 30, 32–33, 305
  See application file for complete search history.

(56) References Cited

U.S. PATENT DOCUMENTS

| | | | |
|---|---|---|---|
| 6,115,862 A | 9/2000 | Cooper et al. | |
| 9,981,052 B2 | 5/2018 | Clynne et al. | |
| 10,736,978 B2 | 8/2020 | Reiber et al. | |
| 10,842,907 B2 | 11/2020 | Goswami et al. | |
| 10,849,997 B2 | 12/2020 | Zhang et al. | |
| 2007/0166213 A1* | 7/2007 | Miller | A61L 2/202 422/300 |
| 2016/0235876 A1* | 8/2016 | Leyva | A61L 2/26 |
| 2017/0151359 A1 | 6/2017 | Clynne et al. | |
| 2018/0055960 A1 | 3/2018 | Reiber et al. | |
| 2019/0046680 A1 | 2/2019 | Goswami et al. | |
| 2020/0114027 A1 | 4/2020 | Zhang et al. | |

* cited by examiner

*Primary Examiner* — Monzer R Chorbaji
(74) *Attorney, Agent, or Firm* — Hamre, Schumann, Mueller & Larson, P.C.

(57) ABSTRACT

The disclosure relates to sterilization and disinfection application, particularly, to equipment capable of disinfecting a ventilator as well as a face mask and a hose, and more particularly, to an ozone disinfection device for actively removing ozone, an ozone disinfection system, and an ozone disinfection method. An ozone disinfection device for actively removing ozone and an ozone disinfection system are provided. An ozone disinfection device includes: a sealed disinfection chamber, a gas distribution unit, an ozone generator, a suction pump, a filter, and a control module.

23 Claims, 8 Drawing Sheets

OZONE DISINFECTION DEVICE FOR ACTIVELY REMOVING OZONE, OZONE DISINFECTION SYSTEM, AND OZONE DISINFECTION METHOD

TECHNICAL FIELD

The disclosure relates to the technical field of sterilization and disinfection application, particularly, to equipment capable of disinfecting a ventilator as well as a face mask and a hose, and more particularly, to an ozone disinfection device for actively removing ozone, an ozone disinfection system, and an ozone disinfection method.

BACKGROUND

At present, ozone disinfection is a commonly used method for disinfecting medical equipment, catering tableware, food processing, etc. Ozone disinfection has many advantages, such as good sterilization effect, complete diffusion to every corners in the space, low cost, environmental protection, and harmlessness to a human body after a small amount of inhalation.

However, ozone disinfection is not perfect and has its own shortcomings. That is because many disinfection products on the market use ozone to sterilize and disinfect items to be disinfected in an enclosed space, and a certain ozone concentration needs to be reached to achieve the disinfection effect. The decay of remaining ozone after disinfection takes some time. After the sterilization and disinfection process is completed, there is still a large amount of ozone remaining in the enclosed space. If no measures are taken to recycle and remove all the remaining ozone, the disinfected items will often be accompanied by a pungent and unpleasant smell, and a large amount of inhalation will also harm human health.

The mainstream solution on the market to this problem is to place consumables such as activated carbon inside a disinfection device, but the activated carbon needs to be replaced regularly, which will increase a user's cost and the use inconvenience. In addition, when the disinfection device is used to disinfect the inside of equipment (for example, a ventilator) to be disinfected, activated carbon cannot remove the odor of ozone remaining in a hose connected to the equipment to be disinfected and inside the equipment to be disinfected. Secondly, the time and effect of deodorizing with activated carbon are not ideal, and activated carbon will occupy the limited space inside the disinfection device.

SUMMARY

A technical problem to be solved by the disclosure is to provide an ozone disinfection device for actively removing ozone, which may quickly filter and evacuate ozone remaining inside the ozone disinfection device and inside equipment to be disinfected (for example, a ventilator) after disinfection is completed, thereby eliminating the ozone remaining inside the ozone disinfection device and inside the equipment to be disinfected at a high speed while not causing ozone pollution to the surrounding environment.

In order to solve the above technical problem, the technical solution adopted by the disclosure is to provide an ozone disinfection device for actively removing ozone, which includes:

a sealed disinfection chamber configured to receive an item to be disinfected or temporarily store ozone, the sealed disinfection chamber communicating with a vent hole;

a gas distribution unit comprising a first interface, a second interface, and a third interface that communicate with each other, the third interface communicating with the vent hole;

an ozone generator configured to generate ozone and inject the generated ozone into the sealed disinfection chamber through the first interface of the gas distribution unit;

a suction pump configured to pump the remaining ozone after disinfection from the sealed disinfection chamber and expel it to the outside, a gas inlet of the suction pump communicating with the sealed disinfection chamber through the second interface of the gas distribution unit, and an exhaust hole of the suction pump communicating with the outside;

a filter connected to the suction pump and configured to eliminate the ozone flowing into or out of the suction pump; and a control module configured to connect and control the operation of the ozone generator and the suction pump.

By using the above technical solution, the first interface of the gas distribution unit may be connected to the ozone generator through a first pipeline, and the second interface of the gas distribution unit may be connected to the suction pump through a third pipeline. The ozone generated by the ozone generator is distributed into the sealed disinfection chamber through the gas distribution unit to disinfect an item to be disinfected placed in the sealed disinfection chamber. After disinfection is completed, the suction pump is activated, the ozone remaining in the sealed disinfection chamber and the first and third pipelines may be pumped to the filter connected to the suction pump, and the filter eliminates the ozone flowing through and then evacuates, so as to eliminate the internal odor of the ozone disinfection device while not causing ozone pollution to the surrounding environment.

As a solution of the ozone disinfection device provided by the disclosure, the filter is connected between the gas inlet of the suction pump and the second interface of the gas distribution unit. That is, after the suction pump is activated, the ozone remaining in the sealed disinfection chamber and the first and third pipelines first flows into the filter for elimination treatment, then flows through the suction pump, and finally is evacuated.

As another solution of the ozone disinfection device provided by the disclosure, the filter is connected to the exhaust hole of the suction pump. Here, after the suction pump is activated, the ozone remaining in the sealed disinfection chamber and the first and third pipelines first flows through the suction pump and then flows into the filter. The filter eliminates the ozone and then evacuates.

As an improvement of the ozone disinfection device provided by the disclosure, the filter is filled with particulate matters for catalytic ozone decomposition.

Through the above improvement, the ozone flowing through the filter will be quickly decomposed into non-polluting oxygen under the action of the particulate matters to ensure the environmental protection of the ozone disinfection device.

As an improvement of the ozone disinfection device provided by the disclosure, the gas distribution unit has a fourth interface communicating with the first interface, the second interface, and the third interface, and the fourth interface is configured to communicate with equipment to be disinfected through a hose to be disinfected.

Through the above improvement, the ozone generated by the ozone generator may also be distributed to the interior of the equipment to be disinfected through the gas distribution unit, thereby disinfecting the equipment to be disinfected (for example, medical equipment such as a ventilator). Similarly, after disinfection is completed, the suction pump is activated, and the ozone remaining in the equipment to be disinfected and the hose to be disinfected may be eliminated by the filter and then expelled out of the equipment to be disinfected, so as to achieve the purpose of eliminating the ozone and odor remaining in the disinfected item while not causing ozone pollution to the surrounding environment of the equipment to be disinfected.

As an improvement of the ozone disinfection device provided by the disclosure, the ozone disinfection device further includes a sealing plug. The gas distribution unit has a fourth interface communicating with the first interface, the second interface, and the third interface. The sealing plug is configured to plug the fourth interface.

Through the above improvement, the ozone disinfection device may realize switching between use modes. Specifically, when it is only necessary to disinfect the item to be disinfected placed in the sealed disinfection chamber, the sealing plug may be used to plug the fourth interface. When the equipment to be disinfected needs to be disinfected, it is only necessary to pull out the sealing plug, and then connect the fourth interface to the equipment to be disinfected.

As an improvement of the ozone disinfection device provided by the disclosure, the gas distribution unit includes: an outer circumferential wall, a partition plate with an edge connected to an inner side of the outer circumferential wall, and an inner circumferential wall with one end connected to the partition plate. The partition plate partitions an inner space of the outer circumferential wall into a first cavity and a second cavity. The inner circumferential wall is located in the second cavity. The partition plate has a central blocking portion located on an inner side of the inner circumferential wall and a peripheral blocking portion located between the inner circumferential wall and the outer circumferential wall. The central blocking portion is provided with a plurality of through holes so that an inner space of the inner circumferential wall communicates with the first cavity. The first cavity and the outer circumferential wall form the third interface. The inner circumferential wall and the central blocking portion form the fourth interface. The second interface is connected to a part of the outer circumferential wall surrounding the first cavity. The second interface communicates with the first cavity directly. The first interface is connected to the part of the outer circumferential wall surrounding the first cavity. The first interface communicates with the first cavity directly.

As an improvement of the ozone disinfection device provided by the disclosure, the ozone disinfection device includes an inner shell and an upper cover. The inner shell includes a box with an upper opening. The upper cover is configured to uncover or cover the opening. A side wall of the box is provided with a safety switch electrically connected to the control module. The safety switch is configured to be switched on when sensing that the upper cover covers the opening, and be switched off when sensing that the upper cover uncovers the opening.

Through the above improvement, the ozone disinfection device will work only when the upper cover covers. When the upper cover uncovers, the ozone disinfection device will automatically stop. Therefore, continuous leakage of ozone caused by accidental uncovering of the upper cover is prevented.

As an improvement of the ozone disinfection device provided by the disclosure, the ozone disinfection device further includes an outer shell with an upper opening. The inner shell, the ozone generator, and the suction pump are all received in the outer shell. A side wall of the outer shell is provided with a circular through hole corresponding to the fourth interface. The upper cover is rotatably connected to the upper opening of the outer shell.

Through the above improvement, the ozone disinfection device has strong integrity and attractive appearance.

As an improvement of the ozone disinfection device provided by the disclosure, the control module includes a display screen for displaying work progress. The display screen is disposed on an inner side of the outer shell. A light transmission area is disposed at a position of the outer shell corresponding to the display screen.

Through the above improvement, a user can better understand the operation progress of the ozone disinfection device.

As an improvement of the ozone disinfection device provided by the disclosure, the side wall of the outer shell is provided with a circular through hole. The fourth interface is exposed from the outer shell through the circular through hole.

Through the above improvement, the fourth interface is exposed from the outer shell to facilitate the insertion and pulling of the sealing plug, thereby improving the efficiency of use mode switching.

The disclosure also provides an ozone disinfection system, which includes: equipment to be disinfected, an item to be disinfected, and the ozone disinfection device as described above.

The equipment to be disinfected includes at least a ventilator and a hose to be disinfected.

The item to be disinfected includes at least a face mask.

Two opposite ends of the hose to be disinfected communicate with the ventilator and the gas distribution unit respectively.

The face mask is received in the sealed disinfection chamber.

In the ozone disinfection system provided by the disclosure, the gas distribution unit includes a first interface, a second interface, a third interface, and a fourth interface that communicate with each other. The first interface communicates with the ozone generator. The second interface communicates with the suction pump. The third interface communicates with the vent hole. The fourth interface communicates with the hose to be disinfected.

In the ozone disinfection system provided by the disclosure, the hose to be disinfected communicates with a gas outlet of the ventilator.

In the ozone disinfection system provided by the disclosure, a gas inlet of the ventilator is plugged by a sealing plug.

In the ozone disinfection system provided by the disclosure, the gas distribution unit includes: an outer circumferential wall, a partition plate with an edge connected to an inner side of the outer circumferential wall, and an inner circumferential wall with one end connected to the partition plate. The partition plate partitions an inner space of the outer circumferential wall into a first cavity and a second cavity. The inner circumferential wall is located in the second cavity. The partition plate has a central blocking portion located on an inner side of the inner circumferential wall and a peripheral blocking portion located between the inner circumferential wall and the outer circumferential wall. The central blocking portion is provided with a plurality of through holes so that an inner space of the inner circumferential wall communicates with the first cavity. The first cavity and the outer circumferential wall form the third interface. The inner circumferential wall and the central blocking portion form the fourth interface. The second interface is connected to a part of the outer circumferential wall surrounding the first cavity. The second interface communicates with the first cavity directly. The first interface is connected to the part of the outer circumferential wall surrounding the first cavity. The first interface communicates with the first cavity directly.

The disclosure further provides another ozone disinfection system, which includes: an item to be disinfected and the ozone disinfection device as described above. The item to be disinfected includes at least a face mask. The face mask is received in the sealed disinfection chamber. The gas distribution unit includes a first interface, a second interface, a third interface, and a fourth interface that communicate with each other. The first interface communicates with the ozone generator. The second interface communicates with the suction pump. The third interface communicates with the vent hole. The fourth interface is plugged by a sealing plug.

In the ozone disinfection system provided by the disclosure, the gas distribution unit includes: an outer circumferential wall, a partition plate with an edge connected to an inner side of the outer circumferential wall, and an inner circumferential wall with one end connected to the partition plate. The partition plate partitions an inner space of the outer circumferential wall into a first cavity and a second cavity. The inner circumferential wall is located in the second cavity. The partition plate has a central blocking portion located on an inner side of the inner circumferential wall and a peripheral blocking portion located between the inner circumferential wall and the outer circumferential wall. The central blocking portion is provided with a plurality of through holes so that an inner space of the inner circumferential wall communicates with the first cavity. The first cavity and the outer circumferential wall form the third interface. The inner circumferential wall and the central blocking portion form the fourth interface. The second interface is connected to a part of the outer circumferential wall surrounding the first cavity. The second interface communicates with the first cavity directly. The first interface is connected to the part of the outer circumferential wall surrounding the first cavity. The first interface communicates with the first cavity directly.

The disclosure further provides an ozone disinfection method. The ozone disinfection method is implemented through the ozone disinfection device as described above and includes the following steps:

placing an item to be disinfected in the sealed disinfection chamber;

activating, by the control module, the ozone generator, ozone from the ozone generator flowing into the sealed disinfection chamber through the gas distribution unit to disinfect the item to be disinfected;

controlling, by the control module, the ozone generator to stop working and activating the suction pump, and pumping, by the suction pump, all the ozone remaining inside the sealed disinfection chamber to the filter; and performing, by the filter, catalytic decomposition treatment on the ozone flowing through, and then evacuating.

In the ozone disinfection method provided by the disclosure, the ozone generator outputs a certain amount of ozone so that the concentration of ozone in the sealed disinfection chamber is not lower than a concentration value capable of killing conventional germs inside a ventilator.

In the ozone disinfection method provided by the disclosure, the gas distribution unit has a fourth interface communicating with the first interface, the second interface, and the third interface. The ozone disinfection method further includes the following step:

plugging the fourth interface using a sealing plug.

The disclosure further provides another ozone disinfection method. The ozone disinfection method is implemented through the ozone disinfection device as described above and includes the following steps:

connecting equipment to be disinfected to the gas distribution unit and the sealed disinfection chamber respectively;

activating, by the control module, the ozone generator, ozone from the ozone generator flowing into the equipment to be disinfected and the sealed disinfection chamber in sequence through the gas distribution unit to disinfect the equipment to be disinfected and the item to be disinfected;

controlling, by the control module, the ozone generator to stop working and activating the suction pump, and pumping, by the suction pump, all the ozone remaining inside the equipment to be disinfected and the sealed disinfection chamber to the filter; and performing, by the filter, catalytic decomposition treatment on the ozone flowing through, and then evacuating.

In the ozone disinfection method provided by the disclosure, the ozone generator outputs a certain amount of ozone so that the concentration of ozone in the equipment to be disinfected and the sealed disinfection chamber is not lower than a concentration value capable of killing conventional germs inside a ventilator.

The ozone disinfection device provided by the disclosure may be implemented to achieve the following beneficial effects.

1. Ozone generated by the ozone generator is distributed into the sealed disinfection chamber through the gas distribution unit to disinfect an item to be disinfected placed in the sealed disinfection chamber. After disinfection is completed, the suction pump is activated, the ozone remaining in the sealed disinfection chamber and the first and second pipelines may be pumped to the filter connected to the suction pump, and the filter eliminates the ozone flowing through and then evacuates, so as to eliminate the internal odor of the ozone disinfection device while not causing ozone pollution to the surrounding environment.

2. The ozone generated by the ozone generator may also be distributed to the interior of the equipment to be disinfected through the gas distribution unit, thereby disinfecting the equipment to be disinfected. Similarly, after disinfection is completed, the suction pump is activated, and the ozone remaining in the equipment to be disinfected and the hose to be disinfected may be expelled out of the equipment to be disinfected, so as to achieve the purpose of eliminating the internal odor of the equipment to be disinfected while not causing ozone pollution to the surrounding environment of the equipment to be disinfected. The equipment to be disinfected may be medical equipment such as a ventilator, or other equipment on the market that requires ozone disinfection and odor elimination.

3. By designing the sealing plug for plugging the fourth interface, the ozone disinfection device may be switched between different use modes, so that one machine may be used for two purposes (disinfecting equipment to be disinfected or disinfecting an item to be disinfected), and the switching is fast and convenient.

4. The structural design of the gas distribution unit fully considers factors such as the smoothness of gas flow and the level of gas pressure, so as to maximize the exhaust effect and facilitate the smooth expelling of the remaining ozone.

5. The safety switch may achieve the effect as follows: the ozone disinfection device will work only when the upper cover covers, and the ozone disinfection device will automatically stop when the upper cover uncovers. Therefore, continuous leakage of ozone caused by accidental uncovering of the upper cover is prevented.

6. By designing the display screen and disposing the light transmission area at a position of the outer shell corresponding to the display screen, a user can better understand the operation progress of the ozone disinfection device.

BRIEF DESCRIPTION OF THE DRAWINGS

In order to more clearly explain the embodiments of the disclosure or the technical solutions in the prior art, the drawings to be used in the description of the embodiments or the prior art will be briefly introduced below. Obviously, the drawings in the following description are only embodiments of the disclosure. For those of ordinary skill in the art, other drawings may be obtained according to the provided drawings without any creative work.

Figure 1:
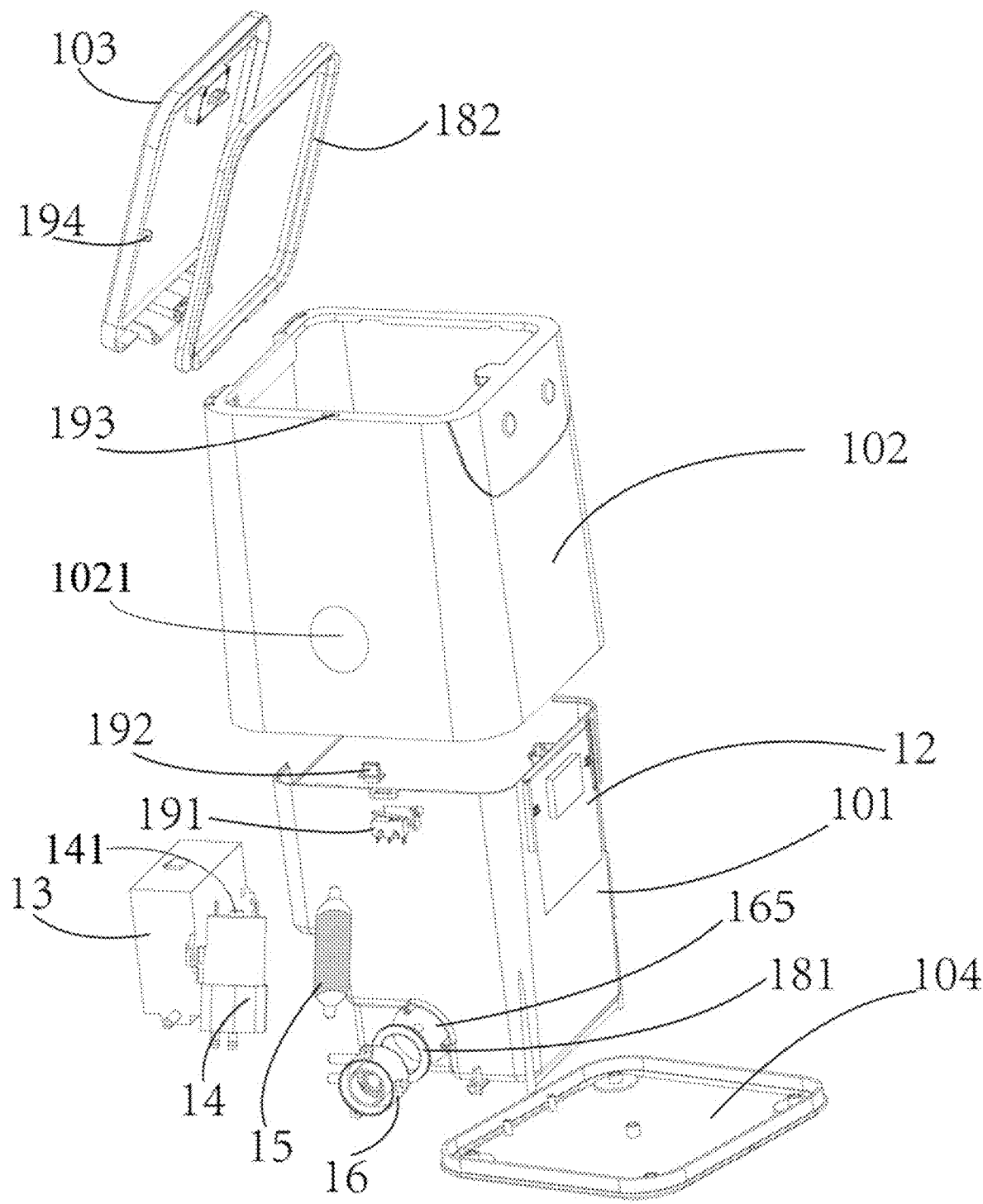
FIG. 1 is a three-dimensional exploded view of an ozone disinfection device provided by the disclosure.

DESCRIPTION OF DRAWING REFERENCE
NUMBERS IN DETAILED DESCRIPTION

| Ozone disinfection device | 100 | Item to be disinfected | 200 |
| --- | --- | --- | --- |
| Equipment to be disinfected | 300 | | |
| Sealed disinfection chamber | 11 | Control module | 12 |
| Ozone generator | 13 | Suction pump | 14 |
| Filter | 15 | Gas distribution unit | 16 |
| Inner shell | 101 | Outer shell | 102 |
| Upper cover | 103 | Bottom cover | 104 |
| First interface | 161 | Second interface | 162 |
| Third interface | 163 | Fourth interface | 164 |
| Vent hole | 165 | Sealing plug | 166 |
| First pipeline | 171 | Second pipeline | 172 |
| Third pipeline | 173 | Second sealing ring | 182 |
| First sealing ring | 181 | Elastic block | 192 |
| Safety switch | 191 | Pushing block | 194 |
| Fixing hole | 193 | Circular through hole | 1021 |
| Exhaust hole | 141 | | |

DETAILED DESCRIPTION

In order to facilitate understanding of the disclosure, the disclosure will be described more comprehensively below with reference to related drawings. Typical embodiments of the disclosure are given in the drawings. However, the disclosure may be implemented in many different forms, which are not limited to the embodiments described herein. On the contrary, the purpose of providing these embodiments is to make the summary of the disclosure more thorough and comprehensive.

It should be noted that if there is a directional indicator (such as up, down, left, right, front, and back . . . ) in the embodiments of the disclosure, the directional indicator is only used to explain content including a relative positional relationship and movement of components in a specific posture (as shown in the figures). If the specific posture changes, the directional indicator will also change accordingly.

Unless otherwise defined, all technical and scientific terms used herein have the same meaning as commonly understood by those skilled in the technical field of the disclosure. The terms used in the specification of the disclosure herein is for the purpose of describing specific embodiments, and are not intended to limit the disclosure.

The terms including ordinal numbers such as "first" and "second" used in this specification may be used to describe various constituent elements, but these constituent elements are not limited by these terms. The purpose of using these terms is only to distinguish one constituent element from other constituent elements. For example, without departing from the scope of the disclosure, the first constituent element may be named as the second constituent element, and similarly, the second constituent element may be named as the first constituent element.

Embodiment I

It is to be first noted that an ozone disinfection device 100 provided in the present embodiment may be used for ozone disinfection of an item to be disinfected 200 or ozone disinfection of the interior of equipment to be disinfected 300. Here, the item to be disinfected 200 may be, but is not limited to, an accessory (a ventilator, a ventilator hose, a ventilator face mask, etc.) of a ventilator or tableware or clothing and bedding, and the equipment to be disinfected 300 may be, but is not limited to, medical equipment such as a ventilator.

Figure 2:
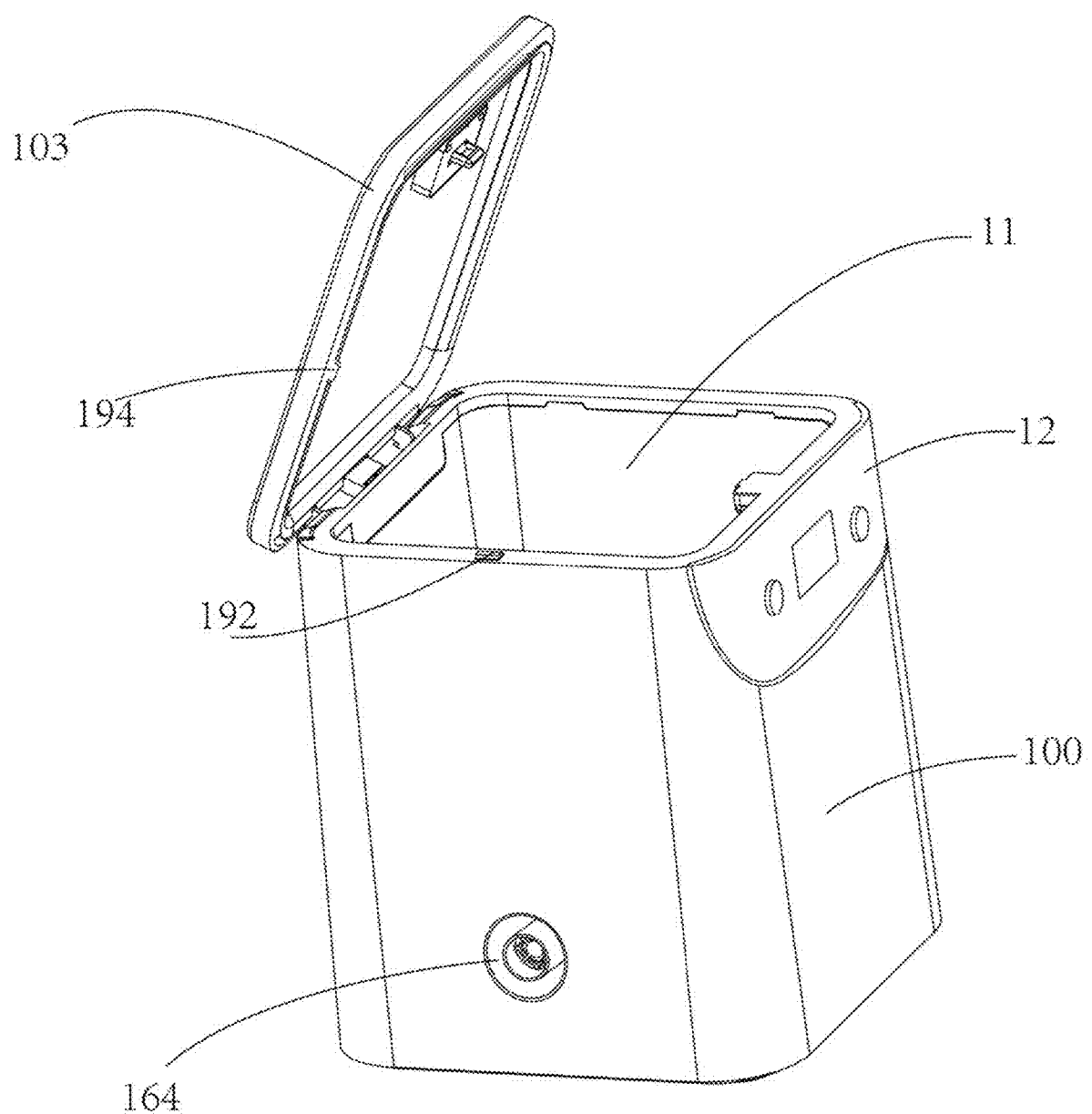
FIG. 2 is a three-dimensional assembly view of an ozone disinfection device provided by the disclosure.

In the present embodiment, referring to FIG. 1 and FIG. 2, the ozone disinfection device 100 includes: a sealed disinfection chamber 11, a gas distribution unit 16, an ozone generator 13, a filter 15, a control module 12, and a suction pump 14. The sealed disinfection chamber 11 is configured to receive the item to be disinfected 200 or temporarily store ozone. The sealed disinfection chamber 11 communicates with a vent hole 165. The gas distribution unit 16 includes a first interface 161, a second interface 162, a third interface 163, and a fourth interface 164 that communicate with each other. The third interface 163 communicates with the vent hole 165. The ozone generator 13 is configured to generate ozone and inject the generated ozone into the sealed disinfection chamber 11 through the first interface 161 of the gas distribution unit 16. The first interface 161 is connected to the ozone generator 13 through a first pipeline 171. The suction pump 14 is configured to pump the remaining ozone after disinfection from the sealed disinfection chamber 11 to the filter 15 to be filtered and expelled to the outside. A gas inlet of the suction pump communicates with the sealed disinfection chamber 11 through the second interface 162 of the gas distribution unit 16. An exhaust hole of the suction pump communicates with the outside. The filter 15 is connected to the suction pump 14 and configured to eliminate the ozone flowing into or out of the suction pump 14. The control module 12 is configured to connect and control the operation of the ozone generator 13 and the suction pump 14.

In the present embodiment, the filter 15 is connected between the gas inlet of the suction pump 14 and the second interface 162 of the gas distribution unit 16. The filter 15 is connected to the second interface 162 through a third pipeline 173, and the filter 15 is connected to the suction pump 14 through a second pipeline 172. In addition, the gas distribution unit 16 further has a fourth interface 164 communicating with the first interface 161, the second interface 162, and the third interface 163. The fourth interface 164 is configured to communicate with the equipment to be disinfected 300 through a hose to be disinfected.

In the present embodiment, the filter 15 is filled with particulate matters for catalytic ozone decomposition. The particulate matters may be manganese oxide.

Figure 3:
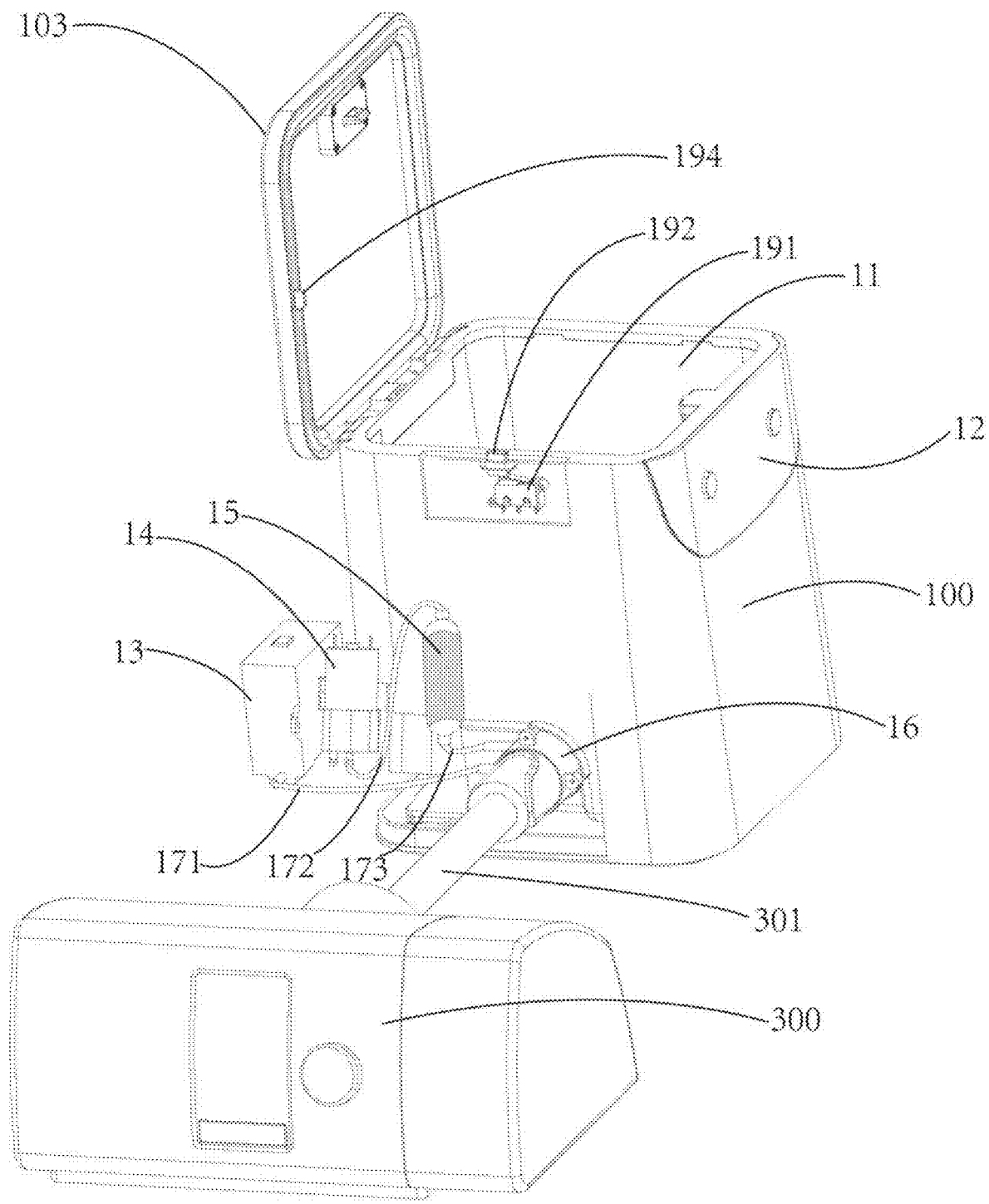
FIG. 3 is a use state reference diagram of an ozone disinfection device provided by the disclosure, wherein the ozone disinfection device is hermetically connected to equipment to be disinfected through a hose to be disinfected, and ozone disinfection may be performed on an item to be disinfected and the equipment to be disinfected simultaneously in this state.
Figure 4:
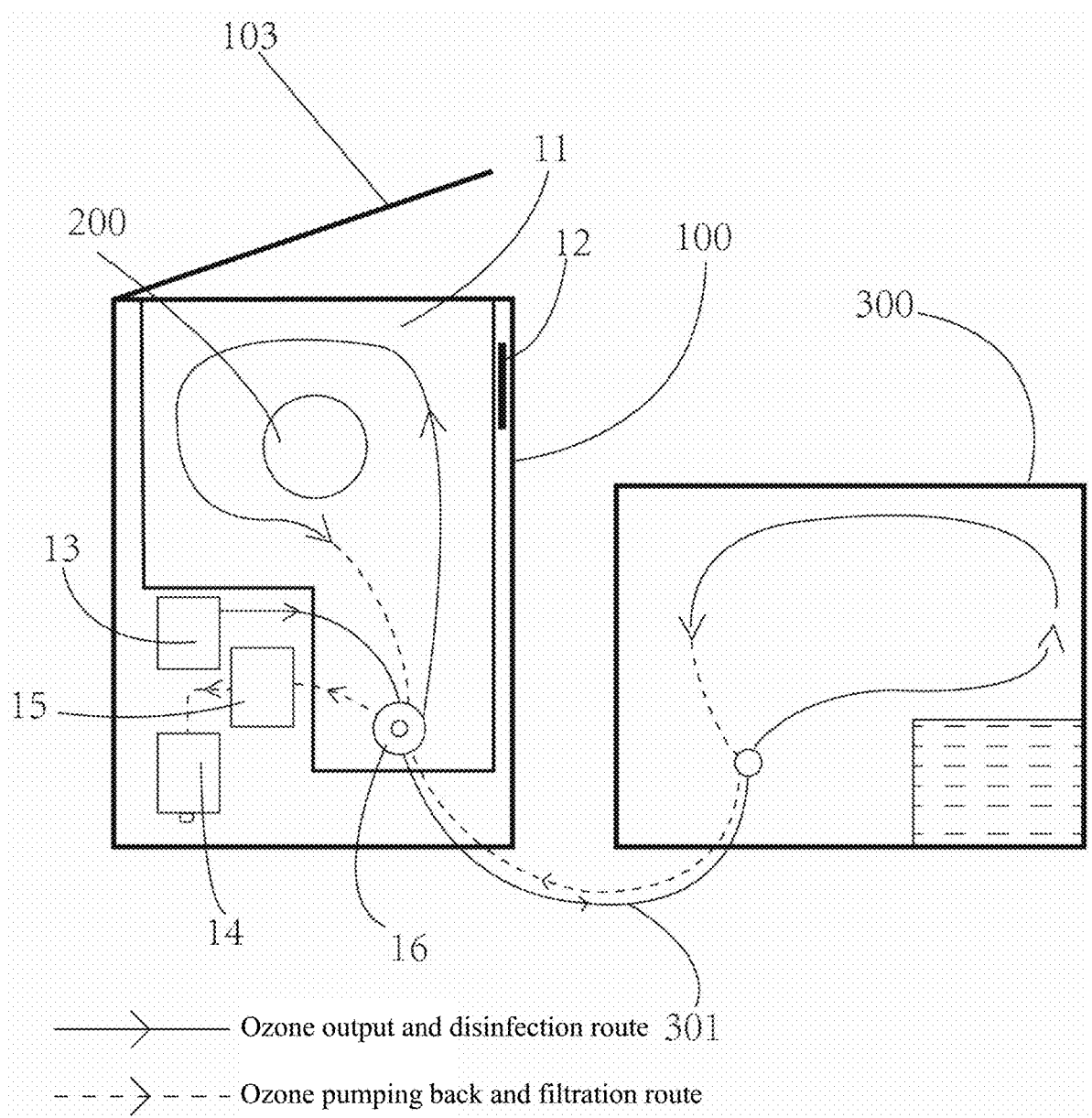
FIG. 4 is a simple view of an ozone disinfection device provided by the disclosure in the state of FIG. 3.

Referring to FIG. 3, when using the ozone disinfection device 100 to simultaneously disinfect the item to be disinfected 200 and the equipment to be disinfected 300 (a ventilator), the item to be disinfected 200 is placed in the sealed disinfection chamber 11 (as shown in FIG. 4), the upper cover 103 covers, and the equipment to be disinfected 300 is connected to the fourth interface 164 through a hose to be disinfected 301. Referring to FIG. 4, lines and arrows are mainly used in FIG. 4 for easy understanding. The solid line represents a path through which ozone is output by the ozone generator 13 for disinfection, and the dotted line represents a path through which ozone is pumped back by the suction pump 14 for filtration and decomposition. It can be clearly seen that the ozone generator 13, the suction pump 14, and the filter 15 are mounted in an interlayer between an outer shell 102 and an inner shell 101. During the operation of the ozone disinfection device 100, the control module 12 issues an instruction to activate the ozone generator 13, and ozone generated by the ozone generator 13 first reaches the gas distribution unit 16, and then is distributed through the gas distribution unit 16. A part of the ozone enters the sealed disinfection chamber 11 while another part of the ozone enters the ventilator along the hose to be disinfected (the shadow in the ventilator is water, and if there is water in a tank of the ventilator, ozone cannot penetrate to the bottom of the tank). After disinfection is completed, the ozone generator 13 stops working, the control module 12 issues an instruction to the suction pump 14, the suction pump 14 starts working to generate a strong negative pressure, the ozone inside the sealed disinfection chamber 11 and the ventilator is pumped back the same way along the gas distribution unit 16, all the ozone will be pumped back to the filter 15, and an ozone oxidant filled in the filter 15 will quickly decompose the ozone, so no ozone will be included in the exhaust gas from the suction pump 14.

Figure 5:
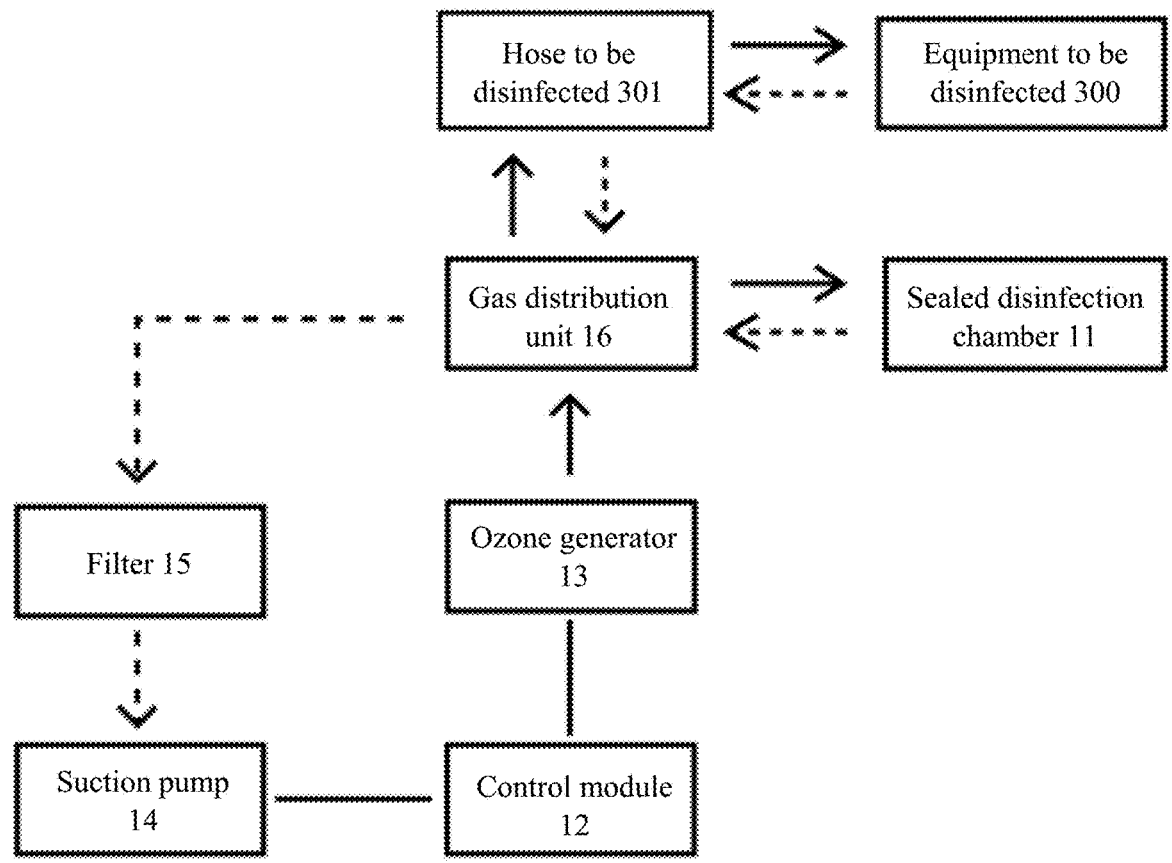
FIG. 5 is a schematic diagram of an ozone disinfection device provided by the disclosure.

It can be seen from the above that the ozone disinfection device 100 is performing ozone disinfection on the item to be disinfected 200 and the equipment 300 to be disinfected (referring to FIG. 5, the solid line segment in FIG. 5 represents a circuit control line, the solid arrow represents an ozone output and disinfection route, and the dotted line segment represents an ozone pumping back and filtration route):

On the one hand, the ozone generated by the ozone generator 13 is distributed into the sealed disinfection chamber 11 through the gas distribution unit 16 to disinfect the item to be disinfected 200 placed in the sealed disinfection chamber 11. After disinfection is completed, the suction pump 14 is activated, the ozone remaining in the sealed disinfection chamber 11, the first pipeline 171 and the third pipeline 173 may be pumped and enter the filter 15. The particulate matters in the filter 15 perform catalytic decomposition on the ozone into non-polluting oxygen, which is finally expelled out of the sealed disinfection chamber 11 through the exhaust hole of the suction pump 14, thereby eliminating the internal odor of the ozone disinfection device 100.

On the other hand, the ozone generated by the ozone generator 13 may also be distributed to the interior of the equipment to be disinfected 300 through the gas distribution unit 16, thereby disinfecting the equipment to be disinfected 300 (for example, medical equipment such as a ventilator). Similarly, after disinfection is completed, the suction pump 14 is activated, the ozone remaining in the equipment to be disinfected 300 and a hose to be disinfected may be expelled into the filter 15. The particulate matters in the filter 15 perform catalytic decomposition on the ozone into non-polluting oxygen, which is finally expelled out of the equipment to be disinfected 300 through the exhaust hole 141 of the suction pump 14, thereby eliminating the internal odor of the equipment to be disinfected 300. More importantly, the ozone remaining in the sealed disinfection chamber 11 and the first pipeline 171 and the third pipeline 173, and the ozone remaining in the equipment to be disinfected 300 and the hose to be disinfected are all catalytically decomposed by the filter 15 and evacuated. Therefore, ozone pollution will not be caused to the external environment.

In summary, the ozone disinfection device 100 may quickly perform ozone disinfection on the item to be disinfected 200 and the equipment to be disinfected 300, and may actively recycle ozone generated in the process of decomposition and disinfection to protect the personal safety of users and the environmental sanitation.

In some other embodiments, the filter 15 may be designed to be connected to the exhaust hole 141 of the suction pump 14. Here, after activating the suction pump 14, the ozone remaining in the sealed disinfection chamber 11, the first pipeline 171 and the third pipeline 173 first flows through the suction pump 14, and then flows into the filter 15. The filter 15 eliminates the ozone and then evacuates.

Figure 6:
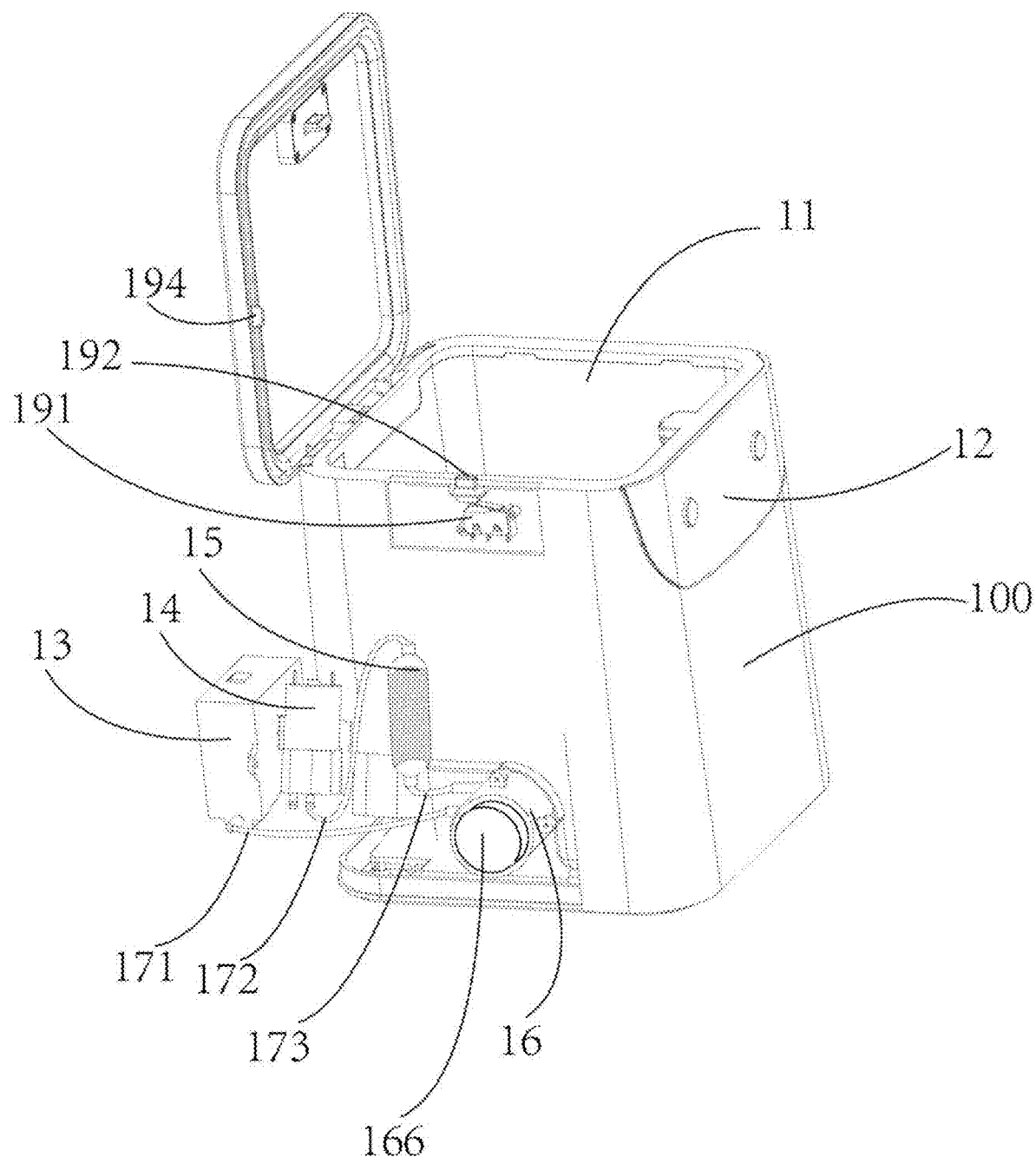
FIG. 6 is another use state reference diagram of an ozone disinfection device provided by the disclosure, wherein ozone disinfection is only performed on an item to be disinfected in this state.

Further, the ozone disinfection device 100 further includes a sealing plug 166. The sealing plug 166 is configured to plug the fourth interface 164. In this way, when it is only necessary to disinfect the item to be disinfected 200 placed in the sealed disinfection chamber 11, the sealing plug 166 may be used to plug the fourth interface 164 so that the ozone generated in the working process may be prevented from escaping from the fourth interface 164 (referring to FIG. 6).

It should be understood by those skilled in the art that, in the disinfection process, the ozone generated by the ozone generator 13 can be quickly injected into the sealed disinfection chamber 11 and the interior of the equipment to be disinfected 300. The ozone generator 13 may be equipped with an electromagnetic pump or a blower fan, thereby improving the work efficiency.

Figure 7:
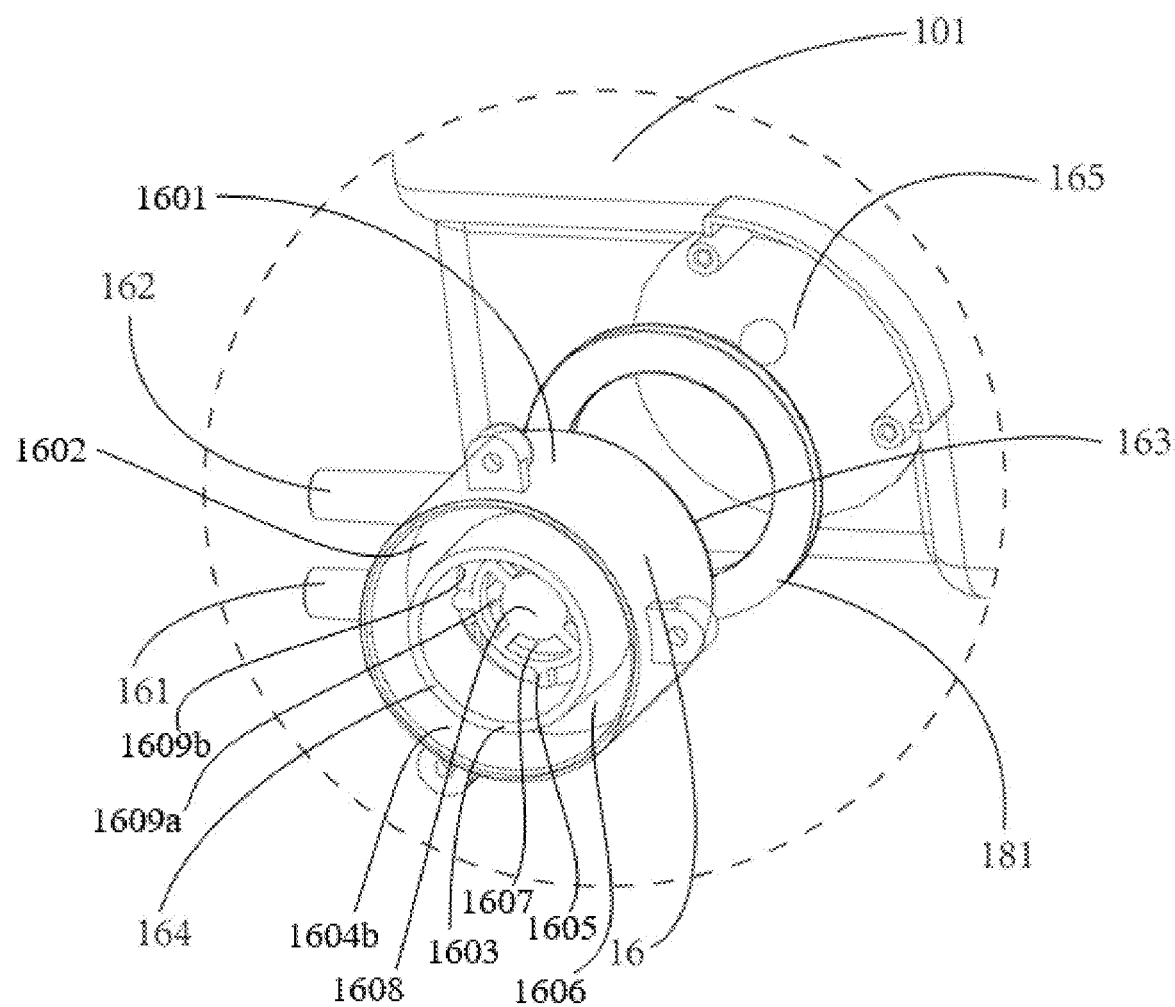
FIG. 7 is a partial enlarged view of FIG. 1.
Figure 8:
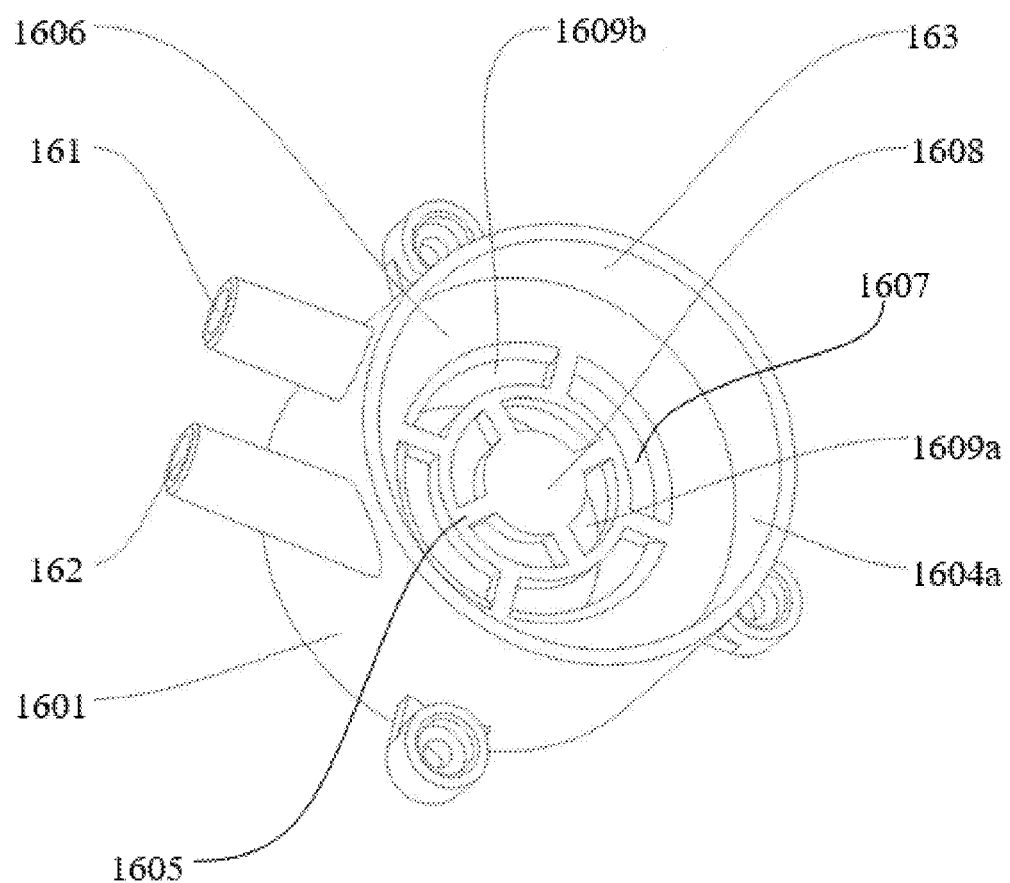
FIG. 8 is a schematic structural view of a gas distribution unit of an ozone disinfection device provided by the disclosure.

In the present embodiment, referring to FIG. 7 and FIG. 8, the gas distribution unit 16 includes: an outer circumferential wall 1601, a partition plate 1602 with an edge connected to an inner side of the outer circumferential wall 1601, and an inner circumferential wall 1603 with one end connected to the partition plate 1602. The partition plate 1602 partitions an inner space of the outer circumferential wall 1601 into a first cavity 1604a and a second cavity 1604b. The inner circumferential wall 1603 is located in the second cavity 1604b. The partition plate 1602 has a central blocking portion 1605 located on an inner side of the inner circumferential wall 1603 and a peripheral blocking portion 1606 located between the inner circumferential wall 1603 and the outer circumferential wall 1601. The central blocking portion 1605 is provided with a plurality of through holes 1607 so that an inner space of the inner circumferential wall 1603 communicates with the first cavity 1604a. Referring to FIG. 7, the plurality of through holes 1607 include a central circular vent through hole 1608, a plurality of inner ring arc-shaped through holes 1609a surrounding the circular vent through hole 1608, and a plurality of outer ring arc-shaped through holes 1609b surrounding the circular vent through hole 1608. The peripheral blocking portion 1606 separates the first cavity 1604a from the second cavity 1604b. The first cavity 1604a and the outer circumferential wall 1601 form the third interface 163. The inner circumferential wall and the central blocking portion form the fourth interface 164. The second interface 162 is cylindrical, and is connected to a part of the outer circumferential wall 1601 surrounding the first cavity 1604a. The second interface 162 communicates with the first cavity 1604a directly. The first interface 161 is cylindrical, and is connected to the part of the outer circumferential wall 1601 surrounding the first cavity 1604a. The first interface 161 communicates with the first cavity 1604a directly. Further, referring to FIG. 3 or FIG. 4, the second interface 162 and the first interface 161 are located on the same side and are disposed in parallel to facilitate internal pipeline connection. Furthermore, the third interface 163 and the vent hole 165 are hermetically connected. In the present embodiment, by adding a first sealing ring 181 between the third interface 163 and the vent hole 165 to achieve a sealed connection, gas leakage from a gap between the gas distribution unit 16 and the inner shell 101 is prevented. Of course, in other embodiments, glue or other sealing methods may also be used.

In the present embodiment, referring to FIG. 1, the ozone disinfection device 100 includes an inner shell 101 and an upper cover 103. The inner shell 101 includes a box with an upper opening. The vent hole 165 is provided at a lower part of the box and communicates with the sealed disinfection chamber 11. The upper cover 103 is configured to uncover or cover the opening. A side wall of the box is provided with a safety switch 191 electrically connected to the control module 12. The safety switch 191 is configured to be switched on when sensing that the upper cover 103 covers the opening, and be switched off when sensing that the upper cover 103 uncovers the opening. The ozone disinfection device 100 further includes an outer shell 102 with an upper opening. The inner shell 101, the ozone generator 13 and the suction pump 14 are all received in the outer shell 102. When the upper cover 103 covers the opening, the inner shell 101, the upper cover 103, and the outer shell 102 together surround the sealed disinfection chamber 11. Specifically, referring to FIG. 5 and FIG. 6, an edge of the opening of the box is provided with a fixing hole 193 penetrating up and down and an elastic block 192 disposed in the fixing hole 193 in a manner of moving up and down. The safety switch 191 is a switch that opens with a light touch, which has a metal touch piece. The safety switch 191 is mounted on the side wall of the box and is located directly under the fixing hole 193. The metal touch piece is aligned upward and is in contact with a lower end of the elastic block 192. One side of the upper cover 103 is hinged with the outer shell 102. The upper cover 103 uncovers or covers the opening in a flipping manner. A pushing block 194 is protruded from an edge of the upper cover 103. In the process of turning the upper cover 103 down to cover the opening, the pushing block 194 may be just pressed against the elastic block 192 and push the metal touch piece to cause the safety switch 191 to be switched on. On the contrary, when the upper cover 103 is turned up to uncover the opening, the metal touch piece is no longer subject to the pressure of the pushing block 194 and the elastic block 192, the metal touch piece will spring back, and the power will be switched off. In this way, it may be achieved that the ozone disinfection device 100 will only work when the upper cover 103 covers and the ozone disinfection device 100 will automatically stop when the upper cover 103 uncovers. Therefore, continuous leakage of ozone caused by accidental uncovering of the upper cover 103 is prevented.

In some other embodiments, the safety switch may be a non-contact switch, such as an infrared sensor.

Further, the upper cover 103 is provided with a frame-shaped sealing groove. A matching second sealing ring 182 is fixed in the sealing groove. When the upper cover 103 covers the opening, the second sealing ring 182 may plug the gap between the upper cover 103 and the sealed disinfection chamber 11, so as to prevent the leakage of ozone in the working process. Furthermore, an open button is disposed on an outer side of the upper cover 103 to realize one-hand opening and closing of the upper cover 103.

In the present embodiment, referring to FIG. 1, the ozone disinfection device 100 further includes an outer shell 102 with an upper opening and a bottom cover 104 fixed to the bottom of the outer shell 102. The sealed disinfection chamber 11, the ozone generator 13 and the suction pump 14 are all received in the outer shell 102. A side wall of the outer shell 102 is provided with a circular through hole 1021 corresponding to the fourth interface 164. The fourth interface 164 is exposed from the outer shell 102 through the circular through hole 1021. The outer shell 102 receives other components of the ozone disinfection device 100 together, so that the ozone disinfection device 100 has a strong integrity and an attractive appearance. Moreover, the fourth interface 164 is exposed from the outer shell 102 to facilitate the insertion and pulling of the sealing plug 166, thereby improving the efficiency of use mode switching.

In the present embodiment, a function button electrically connected to the control module 12 is also disposed on the side wall of the outer shell 102. Specifically, the function button includes key I and key II. In the case where the upper cover 103 covers, key II on the right is long pressed to activate the ozone disinfection device 100, and then key I on the left is pressed to activate a default disinfection mode.

Further, the control module 12 includes a display screen for displaying work progress. The display screen is disposed on an inner side of the outer shell 102. A light transmission area is disposed at a position of the outer shell 102 corresponding to the display screen. The display screen is configured to display work progress. When key I on the left is pressed to start disinfection, the display screen will display words 0%-100% to remind the user of the current disinfection progress. The display of 100% on the display screen indicates that the disinfection is completed. Furthermore, a power connector electrically connected to the control module 12 is also disposed on the outer shell 102 to facilitate connection with an external power supply.

In the present embodiment, the light transmission area is a glass plate disposed on the outer shell 102 and corresponding to the outline size of the display screen, so that the user can see information displayed on the display screen through the glass plate.

In some other embodiments, the light transmission area may also be a square through hole on the outer shell 102 that is equivalent to the outline size of the display screen.

Further, the material of the first pipeline 171, the second pipeline 172, the third pipeline 173, and the hose to be disinfected 301 is a hose material, such as silica gel, ethylene-propylene-diene monomer or fluorelastomer, which is convenient for connection and saves the internal space.

Embodiment II

The present embodiment provides an ozone disinfection system, which includes equipment to be disinfected 300, an item to be disinfected 200, and the ozone disinfection device 100 provided in embodiment I. The equipment to be disinfected 300 includes at least a ventilator and a hose to be disinfected 301. The item to be disinfected 200 includes at least a face mask. Two opposite ends of the hose to be disinfected 301 communicate with the ventilator and the gas distribution unit 16 respectively. The face mask is received in the sealed disinfection chamber 11.

In the present embodiment, the gas distribution unit 16 includes a first interface 161, a second interface 162, a third interface 163, and a fourth interface 164 that communicate with each other. The first interface 161 communicates with the ozone generator 13. The second interface 162 communicates with the suction pump 14. The third interface 163 communicates with the vent hole 165. The fourth interface 164 communicates with the hose to be disinfected 301. The hose to be disinfected 301 communicates with a gas outlet of the ventilator. A gas inlet of the ventilator is plugged by a sealing plug.

In the present embodiment, the gas distribution unit 16 includes: an outer circumferential wall 1601, a partition plate 1602 with an edge connected to an inner side of the outer circumferential wall 1601, and an inner circumferential wall 1603 with one end connected to the partition plate 1602. The partition plate 1602 partitions an inner space of the outer circumferential wall 1601 into a first cavity 1604*a* and a second cavity 1604*b*. The inner circumferential wall 1603 is located in the second cavity 1604*b*. The partition plate 1602 has a central blocking portion 1605 located on an inner side of the inner circumferential wall 1603 and a peripheral blocking portion 1606 located between the inner circumferential wall 1603 and the outer circumferential wall 1601. The central blocking portion 1605 is provided with a plurality of through holes 1607 so that an inner space of the inner circumferential wall 1603 communicates with the first cavity 1604*a*. The first cavity 1604*a* and the outer circumferential wall 1601 form the third interface 163. The inner circumferential wall 1603 and the central blocking portion 1605 form the fourth interface 164. The second interface 162 is connected to a part of the outer circumferential wall 1601 surrounding the first cavity 1604*a*. The second interface 162 communicates with the first cavity directly. The first interface 161 is connected to the part of the outer circumferential wall surrounding the first cavity 1604*a*. The first interface 161 communicates with the first cavity 1604*a* directly.

For the work principle of the ozone disinfection system provided by the present embodiment, reference is made to the process of simultaneously disinfecting the item to be disinfected and the equipment to be disinfected using the ozone disinfection device 100 in embodiment I.

Embodiment III

The present embodiment provides an ozone disinfection system, which includes: an item to be disinfected 200 and the ozone disinfection device 100 provided in embodiment I. The item to be disinfected 200 includes at least a face mask. The face mask is received in the sealed disinfection chamber 11. The gas distribution unit 16 includes a first interface 161, a second interface 162, a third interface 163, and a fourth interface 164 that communicate with each other. The first interface 161 communicates with the ozone generator 13. The second interface 162 communicates with the suction pump 14. The third interface 163 communicates with the vent hole 165. The fourth interface 164 is plugged by the sealing plug 166.

In the present embodiment, the gas distribution unit 16 includes: an outer circumferential wall 1601, a partition plate 1602 with an edge connected to an inner side of the outer circumferential wall 1601, and an inner circumferential wall 1603 with one end connected to the partition plate 1602. The partition plate 1602 partitions an inner space of the outer circumferential wall 1601 into a first cavity 1604*a* and a second cavity 1604*b*. The inner circumferential wall 1603 is located in the second cavity 1604*b*. The partition plate 1602 has a central blocking portion 1605 located on an inner side of the inner circumferential wall 1603 and a peripheral blocking portion 1606 located between the inner circumferential wall 1603 and the outer circumferential wall 1601. The central blocking portion 1605 is provided with a plurality of through holes 1607 so that an inner space of the inner circumferential wall 1603 communicates with the first cavity 1604*a*. The first cavity 1604*a* and the outer circumferential wall 1601 form the third interface 163. The inner circumferential wall 1603 and the central blocking portion 1605 form the fourth interface 164. The second interface 162 is connected to a part of the outer circumferential wall 1601 surrounding the first cavity 1604*a*. The second interface 162 communicates with the first cavity directly. The first interface 161 is connected to the part of the outer circumferential wall surrounding the first cavity 1604*a*. The first interface 161 communicates with the first cavity 1604*a* directly.

For the work principle of the ozone disinfection system provided by the present embodiment, reference is made to the process of only performing ozone disinfection on the item to be disinfected using the ozone disinfection device 100 in embodiment I.

Embodiment IV

The disclosure further provides an ozone disinfection method. The ozone disinfection method is implemented through the ozone disinfection device as described above and includes the following steps:

placing an item to be disinfected in the sealed disinfection chamber 11;

activating, by the control module 12, the ozone generator 13, ozone from the ozone generator 13 flowing into the sealed disinfection chamber 11 through the gas distribution unit 16 to disinfect the item to be disinfected;

controlling, by the control module 12, the ozone generator 13 to stop working and activating the suction pump 14, and pumping, by the suction pump 14, all the ozone remaining inside the sealed disinfection chamber 11 to the filter 15;

performing, by the filter 15, catalytic decomposition treatment on the ozone flowing through, and then evacuating.

It should be noted that the ozone generator 13 outputs a certain amount of ozone so that the concentration of ozone in the sealed disinfection chamber 11 is not lower than a concentration value capable of killing conventional germs inside a ventilator.

In the present embodiment, the gas distribution unit has a fourth interface 164 communicating with the first interface, the second interface 162, and the third interface 163. In order to prevent ozone from escaping from the fourth interface, the ozone disinfection method in the present embodiment further includes the following step:

plugging the fourth interface 164 using a sealing plug 166, wherein the sealing plug 166 effectively prevents ozone from escaping from the fourth interface 164.

In the present embodiment, the item to be disinfected includes a face mask. Obviously, when disinfecting the face mask, it is only necessary to put the face mask into the sealed disinfection chamber 11.

Embodiment V

The present embodiment provides an ozone disinfection method. The ozone disinfection method is implemented through the ozone disinfection device provided in embodiment I.

Specifically, the ozone disinfection method includes the following steps:

connecting equipment to be disinfected to the gas distribution unit and the sealed disinfection chamber respectively;

activating, by the control module, the ozone generator 13, ozone from the ozone generator 13 flowing into the equipment to be disinfected and the sealed disinfection chamber 11 in sequence through the gas distribution unit 16 to disinfect the equipment to be disinfected and the item to be disinfected;

controlling, by the control module 12, the ozone generator 13 to stop working and activating the suction pump 14, and pumping, by the suction pump 14, all the ozone remaining inside the equipment to be disinfected and the sealed disinfection chamber 11 to the filter 15;

performing, by the filter 15, catalytic decomposition treatment on the ozone flowing through, and then evacuating.

It should be noted that the ozone generator 13 outputs a certain amount of ozone so that the concentration of ozone in the equipment to be disinfected and the sealed disinfection chamber 11 is not lower than a concentration value capable of killing conventional germs inside a ventilator.

In the present embodiment, the gas distribution unit 16 has a fourth interface 164 communicating with the first interface, the second interface 162, and the third interface 163. The equipment to be disinfected is connected to the gas distribution unit 16 through the fourth interface 164.

In the present embodiment, the item to be disinfected includes a face mask, and the equipment to be disinfected includes a hose and a ventilator. Here, when disinfecting the face mask, the specific process of "connecting equipment to be disinfected to the gas distribution unit 16 and the sealed disinfection chamber respectively" is: putting the face mask into the sealed disinfection chamber 11, and connecting both ends of the hose to a gas outlet of the ventilator and the fourth interface 164 respectively.

The embodiments of the disclosure have been described above with reference to the drawings, but the disclosure is not limited to the above detailed description. The above detailed description is only schematic, not limiting. Under the enlightenment of the disclosure, those of ordinary skill in the art can make many forms without departing from the spirit of the disclosure and the scope of protection of the claims, all of which fall within the protection of the disclosure.

The invention claimed is:

1. An ozone disinfection device for actively removing ozone, comprising:
   a sealed disinfection chamber configured to receive an item to be disinfected or temporarily store ozone, the sealed disinfection chamber communicating with a vent hole;
   a gas distribution unit comprising:
      a first interface, a second interface, and a third interface that communicate with each other, the third interface communicating with the vent hole, and
      an outer circumferential wall, a partition plate with an edge connected to an inner side of the outer circumferential wall, and an inner circumferential wall with one end connected to the partition plate, the partition plate partitioning an inner space of the outer circumferential wall into a first cavity and a second cavity, and the inner circumferential wall located in the second cavity;
   an ozone generator configured to generate ozone and inject the generated ozone into the sealed disinfection chamber through the first interface of the gas distribution unit;
   a suction pump configured to pump the remaining ozone after disinfection from the sealed disinfection chamber and expel it to the outside, a gas inlet of the suction pump communicating with the sealed disinfection chamber through the second interface of the gas distribution unit, and an exhaust hole of the suction pump communicating with the outside;
   a filter connected to the suction pump and configured to eliminate the ozone flowing into or out of the suction pump; and
   a control module configured to connect and control the operation of the ozone generator and the suction pump.

2. The ozone disinfection device for actively removing ozone according to claim 1, wherein the filter is connected between the gas inlet of the suction pump and the second interface of the gas distribution unit.

3. The ozone disinfection device for actively removing ozone according to claim 1, wherein the filter is connected to the exhaust hole of the suction pump.

4. The ozone disinfection device for actively removing ozone according to claim 1, wherein the filter is filled with particulate matters for catalytic ozone decomposition.

5. The ozone disinfection device for actively removing ozone according to claim 1, wherein the gas distribution unit has a fourth interface communicating with the first interface, the second interface, and the third interface, and the fourth interface is configured to communicate with equipment to be disinfected through a hose to be disinfected.

6. The ozone disinfection device for actively removing ozone according to claim 5, wherein the partition plate has a central blocking portion located on an inner side of the inner circumferential wall and a peripheral blocking portion located between the inner circumferential wall and the outer circumferential wall, the central blocking portion is provided with a plurality of through holes so that an inner space of the inner circumferential wall communicates with the first cavity, the first cavity and the outer circumferential wall form the third interface, and the inner circumferential wall and the central blocking portion form the fourth interface.

7. The ozone disinfection device for actively removing ozone according to claim 6, wherein the second interface is connected to a part of the outer circumferential wall surrounding the first cavity, and the second interface communicates with the first cavity directly.

8. The ozone disinfection device for actively removing ozone according to claim 7, wherein the first interface is connected to the part of the outer circumferential wall surrounding the first cavity, and the first interface communicates with the first cavity directly.

9. The ozone disinfection device for actively removing ozone according to claim 1, further comprising a sealing plug, wherein the gas distribution unit has a fourth interface communicating with the first interface, the second interface, and the third interface, and the sealing plug is configured to plug the fourth interface.

10. An ozone disinfection device for actively removing ozone, comprising:
    a sealed disinfection chamber configured to receive an item to be disinfected or temporarily store ozone, the sealed disinfection chamber communicating with a vent hole;
    a gas distribution unit comprising a first interface, a second interface, and a third interface that communicate with each other, the third interface communicating with the vent hole;
    an ozone generator configured to generate ozone and inject the generated ozone into the sealed disinfection chamber through the first interface of the gas distribution unit;
    a suction pump configured to pump the remaining ozone after disinfection from the sealed disinfection chamber and expel it to the outside, a gas inlet of the suction pump communicating with the sealed disinfection chamber through the second interface of the gas distribution unit, and an exhaust hole of the suction pump communicating with the outside;
    a filter connected to the suction pump and configured to eliminate the ozone flowing into or out of the suction pump; and
    a control module configured to connect and control the operation of the ozone generator and the suction pump;
    wherein the ozone disinfection device comprises an inner shell and an upper cover, the inner shell comprises a box with an upper opening, the upper cover is configured to uncover or cover the opening, a side wall of the box is provided with a safety switch electrically connected to the control module, and the safety switch is configured to be switched on when sensing that the upper cover covers the opening, and be switched off when sensing that the upper cover uncovers the opening.

11. The ozone disinfection device for actively removing ozone according to claim 10, further comprising an outer shell with an upper opening, the gas distribution unit having a fourth interface communicating with the first interface, the second interface, and the third interface, wherein the inner shell, the ozone generator and the suction pump are all received in the outer shell, a side wall of the outer shell is provided with a circular through hole corresponding to the fourth interface, and the upper cover is rotatably connected to the upper opening of the outer shell.

12. The ozone disinfection device for actively removing ozone according to claim 11, wherein the control module comprises a display screen for displaying work progress, the display screen is disposed on an inner side of the outer shell, and a light transmission area is disposed at a position of the outer shell corresponding to the display screen.

13. The ozone disinfection device for actively removing ozone according to claim 11, wherein the side wall of the outer shell is provided with a circular through hole, and the fourth interface is exposed from the outer shell through the circular through hole.

14. An ozone disinfection system, comprising:
    equipment to be disinfected comprising a ventilator and a hose to be disinfected;
    an item to be disinfected comprising a face mask; and
    an ozone disinfection device comprising:
        a sealed disinfection chamber configured to receive an item to be disinfected or temporarily store ozone, the sealed disinfection chamber communicating with a vent hole,
        a gas distribution unit comprising:
            a first interface, a second interface, and a third interface that communicate with each other, the third interface communicating with the vent hole, and
            an outer circumferential wall, a partition plate with an edge connected to an inner side of the outer circumferential wall, and an inner circumferential wall with one end connected to the partition plate, the partition plate partitioning an inner space of the outer circumferential wall into a first cavity and a second cavity, and the inner circumferential wall located in the second cavity,
        an ozone generator configured to generate ozone and inject the generated ozone into the sealed disinfection chamber through the first interface of the gas distribution unit,
        a suction pump configured to pump the remaining ozone after disinfection from the sealed disinfection chamber and expel it to the outside, a gas inlet of the suction pump communicating with the sealed disinfection chamber through the second interface of the gas distribution unit, and an exhaust hole of the suction pump communicating with the outside;
        a filter connected to the suction pump and configured to eliminate the ozone flowing into or out of the suction pump, and
        a control module configured to connect and control the operation of the ozone generator and the suction pump,
    wherein two opposite ends of the hose to be disinfected communicate with the ventilator and the gas distribution unit respectively, and
    the face mask is received in the sealed disinfection chamber.

15. The ozone disinfection system according to claim 14, wherein the gas distribution unit has a fourth interface communicating with the first interface, the second interface, and the third interface, and the fourth interface communicates with the hose to be disinfected.

16. The ozone disinfection system according to claim 14, wherein the hose to be disinfected communicates with a gas outlet of the ventilator.

17. The ozone disinfection system according to claim 16, wherein a gas inlet of the ventilator is plugged by a sealing plug.

18. An ozone disinfection system, comprising:
    an item to be disinfected comprising a face mask; and
    an ozone disinfection device comprising:
        a sealed disinfection chamber configured to receive an item to be disinfected or temporarily store ozone, the sealed disinfection chamber communicating with a vent hole, a gas distribution unit comprising:
  a first interface, a second interface, and a third interface that communicate with each other, the third interface communicating with the vent hole, and
  an outer circumferential wall, a partition plate with an edge connected to an inner side of the outer circumferential wall, and an inner circumferential wall with one end connected to the partition plate, the partition plate partitioning an inner space of the outer circumferential wall into a first cavity and a second cavity, and the inner circumferential wall located in the second cavity,
an ozone generator configured to generate ozone and inject the generated ozone into the sealed disinfection chamber through the first interface of the gas distribution unit,
a suction pump configured to pump the remaining ozone after disinfection from the sealed disinfection chamber and expel it to the outside, a gas inlet of the suction pump communicating with the sealed disinfection chamber through the second interface of the gas distribution unit, and an exhaust hole of the suction pump communicating with the outside,
a filter connected to the suction pump and configured to eliminate the ozone flowing into or out of the suction pump, and
a control module configured to connect and control the operation of the ozone generator and the suction pump,
wherein the face mask is received in the sealed disinfection chamber, and the gas distribution unit comprises a fourth interface communicating with the first interface, the second interface, and the third interface and the fourth interface is plugged by a sealing plug.

19. An ozone disinfection method, wherein the ozone disinfection method is implemented using an ozone disinfection device, comprising:
  a sealed disinfection chamber configured to receive an item to be disinfected or temporarily store ozone, the sealed disinfection chamber communicating with a vent hole,
  a gas distribution unit comprising:
    a first interface, a second interface, and a third interface that communicate with each other, the third interface communicating with the vent hole, and
    an outer circumferential wall, a partition plate with an edge connected to an inner side of the outer circumferential wall, and an inner circumferential wall with one end connected to the partition plate, the partition plate partitioning an inner space of the outer circumferential wall into a first cavity and a second cavity, and the inner circumferential wall located in the second cavity,
  an ozone generator configured to generate ozone and inject the generated ozone into the sealed disinfection chamber through the first interface of the gas distribution unit,
  a suction pump configured to pump the remaining ozone after disinfection from the sealed disinfection chamber and expel it to the outside, a gas inlet of the suction pump communicating with the sealed disinfection chamber through the second interface of the gas distribution unit, and an exhaust hole of the suction pump communicating with the outside,
  a filter connected to the suction pump and configured to eliminate the ozone flowing into or out of the suction pump, and
  a control module configured to connect and control the operation of the ozone generator and the suction pump,
the ozone disinfection method comprising:
  placing an item to be disinfected in the sealed disinfection chamber;
  activating, by the control module, the ozone generator, ozone from the ozone generator flowing into the sealed disinfection chamber through the gas distribution unit to disinfect the item to be disinfected;
  controlling, by the control module, the ozone generator to stop working and activating the suction pump, and pumping, by the suction pump, all the ozone remaining inside the sealed disinfection chamber to the filter; and
  performing, by the filter, catalytic decomposition treatment on the ozone flowing through, and then evacuating.

20. The ozone disinfection method according to claim 19, wherein the ozone generator outputs a certain amount of ozone so that the concentration of ozone in the sealed disinfection chamber is not lower than a concentration value capable of killing conventional germs inside a ventilator.

21. The ozone disinfection method according to claim 19, wherein the gas distribution unit has a fourth interface communicating with the first interface, the second interface, and the third interface, and the ozone disinfection method further comprises:
  plugging the fourth interface using a sealing plug.

22. An ozone disinfection method, wherein the ozone disinfection method is implemented using an ozone disinfection device comprising:
  a sealed disinfection chamber configured to receive an item to be disinfected or temporarily store ozone, the sealed disinfection chamber communicating with a vent hole,
  a gas distribution unit comprising:
    a first interface, a second interface, and a third interface that communicate with each other, the third interface communicating with the vent hole, and
    an outer circumferential wall, a partition plate with an edge connected to an inner side of the outer circumferential wall, and an inner circumferential wall with one end connected to the partition plate, the partition plate partitioning an inner space of the outer circumferential wall into a first cavity and a second cavity, and the inner circumferential wall located in the second cavity,
  an ozone generator configured to generate ozone and inject the generated ozone into the sealed disinfection chamber through the first interface of the gas distribution unit,
  a suction pump configured to pump the remaining ozone after disinfection from the sealed disinfection chamber and expel it to the outside, a gas inlet of the suction pump communicating with the sealed disinfection chamber through the second interface of the gas distribution unit, and an exhaust hole of the suction pump communicating with the outside,
  a filter connected to the suction pump and configured to eliminate the ozone flowing into or out of the suction pump, and
  a control module configured to connect and control the operation of the ozone generator and the suction pump, the ozone disinfection method comprising:

connecting equipment to be disinfected to the gas distribution unit and the sealed disinfection chamber respectively;

activating, by the control module, the ozone generator, ozone from the ozone generator flowing into the equipment to be disinfected and the sealed disinfection chamber in sequence through the gas distribution unit to disinfect the equipment to be disinfected and the item to be disinfected;

controlling, by the control module, the ozone generator to stop working and activating the suction pump, and pumping, by the suction pump, all the ozone remaining inside the equipment to be disinfected and the sealed disinfection chamber to the filter; and performing, by the filter, catalytic decomposition treatment on the ozone flowing through, and then evacuating.

23. The ozone disinfection method according to claim 22, wherein the ozone generator outputs a certain amount of ozone so that the concentration of ozone in the equipment to be disinfected and the sealed disinfection chamber is not lower than a concentration value capable of killing conventional germs inside a ventilator.

* * * * *